United States Patent [19]
Jozefowicz et al.

[11] Patent Number: 6,160,056

[45] Date of Patent: Dec. 12, 2000

[54] MOLDING MATERIALS HAVING ANTICOAGULANT PROPERTIES, THEIR PREPARATION AND PROCESSING TO GIVE ARTICLES WHICH ARE USED IN MEDICAL TECHNOLOGY

[75] Inventors: Marcel Jozefowicz, Lamorlaye; Veronique Migonney, Eaubonne, both of France; Heinz Hermann Meyer, Marl, Germany; Thomas Neu, Duelmen, Germany; Axel Stieneker, Muenster, Germany; Christine Anders, Haltern, Germany; Peter Ottersbach, Windeck, Germany

[73] Assignee: Vestolit GmbH, Marl, Germany

[21] Appl. No.: 09/033,070

[22] Filed: Mar. 2, 1998

[30] Foreign Application Priority Data

| Mar. 1, 1997 | [DE] | Germany | 197 08 426 |
| Sep. 26, 1997 | [DE] | Germany | 197 42 528 |
| Feb. 18, 1998 | [DE] | Germany | 198 06 748 |

[51] Int. Cl.$^7$ ................. C08F 2/04; C08F 2/12
[52] U.S. Cl. ................. 525/330.5; 525/331.5; 525/333.1
[58] Field of Search ............. 525/330.5, 331.5, 525/331.1, 332.2

[56] References Cited

U.S. PATENT DOCUMENTS

| 4,468,378 | 8/1984 | Voronkov et al. | 424/78.27 |
| 4,530,964 | 7/1985 | Machovich et al. | 525/61 |
| 4,568,725 | 2/1986 | Boisson et al. | 525/330.5 |
| 5,116,994 | 5/1992 | Ono | 548/251 |
| 5,278,200 | 1/1994 | Coury et al. | 523/112 |

FOREIGN PATENT DOCUMENTS

| 4208165 | 7/1992 | Japan . |

*Primary Examiner*—Robert H. Harrison
*Attorney, Agent, or Firm*—Oblon, Spivak, McClelland, Maier & Neustadt, P.C.

[57] ABSTRACT

A process for preparing molding materials having anticoagulant properties is described. Hydrophobic monomers are subjected to free-radical copolymerization with hydrophilic monomers having biospecifically active functions to produce the molding material. The molding material may then be shaped into articles which also have anticoagulant properties. These articles are extremely useful in, for example, medical applications in contact with a patient's biological fluid.

19 Claims, No Drawings

MOLDING MATERIALS HAVING ANTICOAGULANT PROPERTIES, THEIR PREPARATION AND PROCESSING TO GIVE ARTICLES WHICH ARE USED IN MEDICAL TECHNOLOGY

BACKGROUND OF THE INVENTION

1. Field of the Invention

The present invention relates to the preparation of molding materials having certain bioactive functions, special measures in the processing of these molding materials to provide articles having surface-active bioactive functions and the use of these articles in medical technology, in particular for contact with blood or components thereof.

2. Description of the Related Art

The term "bioactivity" is to be understood herein in the widest sense as meaning the interaction between certain randomly arranged functional groups or combinations of such functional groups in synthetically produced macromolecules and complementary functions of natural macromolecular systems.

The interaction between blood and foreign surfaces, for example polymer surfaces, is well-known. The contact of certain proteins contained in the blood with these foreign surfaces leads to a cascade-like activation of various biochemical secondary reactions which culminate in the so-called complement activation or blood coagulation. Since the 1950s, a wide range of detailed experiments have been carried out in an attempt to influence the interaction between foreign surfaces and blood so that, on temporary or on long-term contact, blood coagulation and disadvantageous reactions of the immune system, such as inflammations, etc., do not occur.

The range of measures is wide and in some cases contradictory, as shown in the following review, c.f. R. Barbucci et al. "Modifications of Polymer Surfaces to Improve Blood Compatibility", page 119 et seq. in: Polymeric Biomaterials, S. Dumitriu Editor, Marcel Dekker Inc., 1994:

(1) Establishment of hydrophobic surfaces
   hydrophobic surfaces after alkylation, hence preferred adsorption of albumin, hence reduction of blood coagulation,
   imparting of hydrophilic properties to polymer surfaces with polyethylene glycol chains, hence reduced protein and blood platelet adsorption;
(2) Production of surfaces having a zwitterionic or anionic structure
   neutral zwitterionic structures, e.g., polymer-bound phosphorylcholine end groups (EP 0 275 295, 1986, A. A. Durrani),
   anionic structures of certain concentration and composition.

The measures according to the invention follow this last-mentioned line of development.

Here, the naturally occurring heparin, a glycosamine glycan having carboxyl, sulfate and aminosulfate groups, has long been preferred. It was bound adsorptively, ionically or covalently to polymer surfaces; however, it was found that its activity declines relatively rapidly and hence the stability required for long-term clinical applications is no longer present. A further development consisted in fixing the heparin functions recognized as bioactive, namely carboxylate and sulfate/sulfonate, to the surfaces of a range of crosslinked polymers or to dissolved polymers by wet chemical polymer-analogous reactions, in order to produce heparin-like behavior in this manner. The work of Jozefowicz and Jozefowicz et al. may be mentioned in particular here, cf. EP-A 0 023 854, 0 090 100, 0 094 893, 0 201 378, 0 203 865 and 0 304 377.

Polymer surfaces can be modified in the manner described above also with the aid of energy sources, such as ionizing radiation or electrical discharges, cf. R. Barbucci et al. loc. cit., page 204 et seq.

Finally, it is also possible to introduce the bioactive functions bound to vinyl monomers into polymer systems by copolymerization or to bind them in a thin polymer layer to polymer surfaces. Examples of this line of development are works by Miller, Sawyer et al., J. Appl. Polym. Sci. 1970, 14, 257–266, by Sorm, Nespurek et al., J. Polym. Sci., Polym. Symp. 1979, 66 349–356, and EP 0 598 486 to MEDTRONIC Inc. (Oct. 14, 1993). In this more recent application, combinations of the monomeric acrylic acid and 2-acrylamido-2-methylpropanesulfonic acid, in particular in a molar ratio of 2:7, are claimed. This monomer mixture is either copolymerized as such and then applied to polymer surfaces, for example by immersion in corresponding solutions, or it is grafted directly onto polymer surfaces in the presence of cerium ions.

A common feature of all processes mentioned, where they relate to solid polymers and surfaces thereof, is that the bioactive functions are fixed to already shaped articles in a further processing step. The disadvantages of such processes are obvious:

(1) The reproducible establishment of identical bioactive surfaces, for example for series production of catheters and blood bags, which is indispensable in human medicine, cannot be guaranteed in this manner.
(2) The subsequent modification is time-consuming and consumptive of material (economy and ecology).
(3) The reusability (recycling) of such surface-modified articles is not possible because the same bioactive surfaces will not be present after a further melting and processing step.

Accordingly, there remains a need for a process which overcomes these disadvantages.

SUMMARY OF THE INVENTION

It is an object of the present invention to provide a process for preparing molding materials having anticoagulant properties, in which hydrophobic monomers are subjected to free-radical copolymerization with hydrophilic monomers having biospecifically active functions, and the use of these molding materials in, for example, medical technology.

It is another object of the present invention to provide a process for making an article having anticoagulant properties by shaping a composition comprising a molding material having anticoagulant properties into the article, where the molding material is obtained by a process comprising free radically copolymerizing at least one hydrophobic monomer and at least one hydrophilic monomer having at least one biospecifically active functional group.

It has been found, surprisingly, that, by free-radical copolymerization of a certain range of suitable vinyl monomers, it is possible to prepare molding materials which have bioactive functions chemically homogeneously distributed from polymer particle to polymer particle an which, depending on concentration and combination of the bioactive function introduced with the vinyl monomers, can be shaped into articles which are widely used in medical technology.

It has also been found that the processing to give articles having surface-active bioactive functions requires particular

DETAILED DESCRIPTION OF THE INVENTION measures in order to distribute these bioactive functions uniformly over the interior and surface regions of the articles or to concentrate them at the surface even after the processing.

A more complete appreciation of the invention and many of the attendant advantages thereof will be readily obtained as the same becomes better understood by reference to the following detailed description.

The present invention provides a method for preparing a molding material (i.e., a polymer resin) having, for example, anticogulant properties. These materials may be prepared by free radically copolymerizing one or more hydrophobic monomers with one or more hydrophilic monomers that have biospecifically active functional groups. Without being limited to any theory, these biospecifically active functional groups may be responsible for imparting the anticogulant properties to the resulting polymer resin material. The anticogulant molding material may be directly shaped into articles having anticogulant properties.

A particularly versatile process for the preparation of the molding materials according to the invention is free-radical copolymerization. This can be carried out by mass polymerization, by solution polymerization with subsequent precipitation or by dispersion polymerization. The copolymerization in dispersion comprises all known processes in which the monomer mixture or parts thereof are present in disperse form in a liquid, stirrable medium. This carrier medium is generally water, but may also be an organic phase. These known methods include suspension polymerization and emulsion polymerization with a water-dispersed organic phase, but also their inverse forms in which the aqueous phase with the water-soluble monomers is dispersed in the organic phase. The special techniques of micro- and mini-emulsion polymerization, too, can be in principle be used for the preparation of the claimed molding materials. Furthermore, solution/precipitation copolymerization of vinyl chloride in alkyl alcohols, such as, for example, methanol, ethanol, propanol or isopropanol, is also possible. The monomers in dispersions are preferably subjected to free-radical copolymerization.

Since the solubilities and reactivities of the monomers which may be used can differ very greatly, the polymerization reactions are most preferably microprocessor-monitored and -controlled so that the incorporation of the bioactive functions takes place completely, and as uniformly as possible in all macromolecules. The techniques, known per se, involving the metered addition of monomer building blocks during the polymerization (feed process) and the polymerization in stages are therefore used, as will be discussed in the Examples below.

The range of the monomers capable of free-radical copolymerization comprises both hydrophobic and hydrophilic monomers, where the latter are, as a rule, provided with bioactive functions. The monomers are preferably vinyl compounds, i.e, contain one or more (preferably one) free radically polymerizable double bond. The hydrophobic monomers used include in particular styrene, methyl methacrylate and vinyl chloride.

The hydrophilic monomers have at least one bioactive functional group useful for imparting the desired anticogulant properties to the polymer resin and the molded article produced therefrom. Preferred hydrophilic monomers are those which carry bioactive base functions, such as hydroxyl, carboxyl and sulfatyl or sulfonyl groups. These include the hydroxyalkyl (meth) acrylates and mono-$(EO)_n$-vinyl ethers and -vinyl esters, acrylic acid and methacrylic acid and maleic acid and maleic anhydride and half-esters derived therefrom and finally vinyl sulfonates in the widest sense, especially vinyl arylsulfonates, such as styrene sulfonate.

Also suitable for use as hydrophilic monomers are monomers which may be regarded as the reaction products of carboxyl- and sulfonyl-containing vinyl monomers described above with amino acids or purine or pyrimidine bases. Owing to their structure, these functionalities are capable of forming specific bonds to proteins, enzymes and living cells when incorporated into the polymer resin.

Some or all of the biospecifically active functions of the hydrophilic monomers may be substituted by further biospecifically active functions to provide monomers represented by the following formulae:

M—$F_1$,

M—$F_2$,

M—$F_3$, and

M—$F_1$–$F_4$, where

M is a radical of the hydrophilic monomer and:

$F_1$ is an alkyl, aryl or alkyl/arylhydroxyl group, $F_2$ is an alkyl, aryl or alkyl/arylcarboxyl group, $F_3$ is an alkyl, aryl or alkyl/arysulfonyl group, and $F_4$ is an alkyl, aryl or alkyl/arylphosphatyl group.

Preferably, the alkyl group in $F_1$–$F_4$ has 1 to 20 carbon atoms, inclusive of all specific values and subranges therebetween; the aryl group in $F_1$–$F_4$ is preferably phenyl. The monomers having biospecifically active functions useful for preparing the molding material may also be represented by the following formulae:

M—$F_2$—$S_1$,

M—$F_3$—$S_1$,

M—$F_1$–$F_4$—$S_1$,

M—$F_1$–$F_4$—$S_2$, and

M—$F_1$–$F_4$—$S_3$, where $S_1$ is the radical of an amino acid which is bound to carboxyl, sulfonyl or phosphatyl functionality of the $F_2$, $F_3$, or $F_4$ group via its —$NH_2$, the preferred amino acids being glutamine, threonine, methionine, cysteine, cysteic acid, proline, hydroxylproline, serine, tyrosine, benzoyloxycarbonyl-lysine, tert-butoxycarbonyl-lysine, ε-aminocaproic acid. β-alanine, γ-amino-n-butyric acid and substituted or unsubstituted δ-amino-n-valeric acid; $S_2$ is a N-hydroxyethylated purine or pyrimidine base or sugar radical-purine or sugar radical-pyrimidine base; and $F_4$—$S_3$ together represent a phospholipid where, for example, $S_3$ represents choline.

Accordingly, the essential feature of the hydrophilic monomer is that it contains at least one ethylenically unsaturated functional group (i.e., a polymerizable carbon-carbon double bond) and at least one biospecifically active functional group, as described above. Such a monomer may be represented by the formula K—X, where K is an organic radical containing an ethylenically unsaturated double bond and X is a biospecifically active functional group (such as hydroxyl, carboxyl and sulfatyl or sulfonyl groups). These monomers may also be represented by the formulae shown below:

K—$F_1$,

K—$F_2$,

K—$F_3$,
K—$F_1$-$F_4$,
K—$F_2$—$S_1$,
K—$F_3$—$S_1$,
K—$F_1$-$F_4$—$S_1$,
K—$F_1$-$F_4$—$S_2$, and
K—$F_1$-$F_4$—$S_3$, where K and the other structural variables are as defined above. The number of carbon atoms in the K group may vary widely, such as 2 to 30, inclusive of all specific values and subranges therebetween (such as 5, 10, 15, 18, 20, 22, and 25). The K group may also contain other atoms, such as oxygen (e.g., in hydroxyl groups, ether groups and/or carboboxyl groups) and/or sulfur (e.g., in sulfatyl and/or sulfonyl groups).

The ratio of the hydrophobic monomers to hydrophilic monomers used to prepare the molding material may vary widely. For example, on the basis of 100 parts by weight of the hydrophobic monomers, 2 to 200 parts by weight of the hydrophilic monomers may be used. Preferably, 5 to 150 parts by weight of the hydrophilic monomers per 100 parts by weight of the hydrophobic monomers are used, more preferably, 10 to 100 parts by weight of the hydrophilic monomers per 100 parts by weight of the hydrophobic monomers, and, most preferably, 15 to 75 parts by weight of the hydrophilic monomers per 100 parts by weight of the hydrophobic monomers. These ranges include all specific values and subranges therebetween, such as 20, 25, 30, 40, 50, 60, 80, 110, 125, and 140 parts by weight of the hydrophilic monomers per 100 parts by weight of the hydrophobic monomers.

The polymer dispersions may be worked up by spray-drying, precipitation, electrophoresis or another form of solid-liquid separation with subsequent drying.

The dry powder alone or as a blend with VC homopolymers (E—, S— or micro-S—PVC), may be processed, with the assistants required for the respective processing and acceptable for the subsequent use, such as stabilizers, lubricants, plasticizers, etc., either via a granular intermediate or directly to give articles for medical applications. The molding materials may be blended with from 5 to 85% by weight of a plasticizer, such as mono- and diesters of dicarboxylic acids and hydroxydicarboxylic acids, expoxidized natural oils, epoxidized fatty acids and their esters and polyesters, and esters of trimellitic acid. Preference is given to dioctyl phthalate, citrates, epoxidized soybean and linseed oils and alkyl epoxysterates having epoxide contents of from 1.5 to 10%.

The shaping of the articles having bioactive surfaces may require special measures, as a simple experiment is to illustrate. If, for example, a vinyl chloride polymer is prepared by one of the processes described above, said polymer is dissolved in tetahydrofiran, the solution is poured into a shallow Petri dish and the solvent is allowed to evaporate, a film is thus obtained. If the distribution of the sulfonate functions on this film is measured perpendicular to the surface with the aid of suitable analytical methods, an inhomogeneous distribution is surprisingly found, namely a lower concentration on the upper surface in contact with air and a higher concentration on the lower surface facing the glass.

Similar results are also obtained with processing, for example, extrusion, to give tubes; for use as catheters. In this case, both surfaces, the inner and the outer surface, have a low concentration of bioactive functions.

Even better results are obtained when the shaping molds are provided with polar surfaces in the regions in which the shaping of the homogeneous melt in to articles takes places with incipient cooling: bioactive functions are uniformly distributed in the inner and outer regions of the article or are even concentrated at the interfaces.

The coating of the surfaces of the shaping molds should have a surface tension of >50 mN/m at the contact surface and can be effected in various ways:

(1) Coating or lining of heat-resistant materials, such as metal alloys or plastics (crosslinked or uncrosslinked), such as, for example, phenol/formaldehyde condensates, nylon-4, nylon-6, nylon-6,6 or ceramic substances, and
(2) Production of continuous water/steam gliding film.

The detection of the bioactivity, especially the anticoagulant behavior of such articles, for example of tubes, may be carried out as follows. The tubes are subjected to 3 wash cycles of 3 hours with 1.5 molar NaCl at 90° C.
3 wash cycles of 3 hours with water at room temperature
1 wash cycle of 12 hours with Michaelis buffer at room temperature in a circulation apparatus (15 ml/min).

Absorption experiments with radioactive-labeled human serum albumin (HSA), $^{125}$I—HSA, are then carried out in order to determine the active surface area. For this purpose, tubes are exposed to a $^{125}$I—HSA buffer solution (3 mg/ml) at room temperature for 40 min, once again in a circulation apparatus (15 ml/min). The radioactivity is then determined on the empty tubes. The specific amount of adsorbed albumin in mg/cm$^2$ of geometric surface area is then obtained from the resulting radioactivity in cpm (counts per minute) divided by the specific radioactivity of the $^{125}$I—HSA in cpm/mg, furthermore divided by the specific surface area in cm$^2$.

Finally, the thrombin (T)-antithrombin (AT) interaction in the presence of the inner tube surfaces is determined. The rate constant $k_{app}$ in ml/(u•min)•10$^3$ (=unites) in the reaction

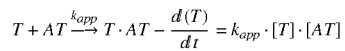

$$T + AT \xrightarrow{k_{app}} T \cdot AT - \frac{d(T)}{dt} = k_{app} \cdot [T] \cdot [AT]$$

is used as a measure of this interaction.

For this purpose, AT in Michaelis buffer (0.2 u/ml) is circulated in a circulation apparatus (15 ml/min) for 30 min. T (1000 u/ml) is then added to the circulating solution in 0.25 ml increments up to a total volume of 5 ml. The T—AT reaction is then monitored at 5 minute intervals by T determination after withdrawal of 0.12 ml of solution. If I/T is plotted against the time, a straight line with the slope $k_{app}$ is obtained.

The antithrombic activity ($k_{kapp}$) of the molded resin may vary The apparent rate constant of the T—AT reaction is preferably at least 2•10$^{-3}$ ml (u•min), more preferably at least 3•10$^{-3}$ ml/(u•min).

The described versatile process for the preparation of molding materials and articles with variable concentration and combination of bioactive functions gives rise to a wide range of potential applications of the resulting articles.

First, the powder obtained according to the invention can be used both in dissolved from and in solid form as a coating medium having an anticoagulant action. Owing to the adjustable bioactive surfaces, the molding materials shaped into articles are suitable for medical and surgical use in the widest sense, for example as tubes, cathethers, blood bags, films, threads, cardiovascular prostheses, etc.

Another possible field is also the use as a stationary phase, in compact form or in a thin layer on a mechanically stable substrate, in all types of chromatographic separation processes for the purification of certain blood components, enzymes, coenzymes or enzymatic complexes. Finally, the claimed systems can also be used for various biological analytical methods, for example in electrophoresis, immunoelectrophoresis, RIA, ELISA, etc.

Having generally described this invention, a further understanding can be obtained by reference to certain specific examples which are provided herein for purposes of illustration only and are not intended to be limiting unless otherwise specified.

EXAMPLES

Example 1 (emulsion polymerization)

In the first stage 88.7 parts of deionized water (all further data in parts are based on the total organic phase=100 parts), 5 parts of maleic acid monobutyl ester (MMBE) and 0.2 parts MARLON A315 (alkyl benzene sulfonate, OXENO Olefinchernie GmbH) as a 15% water solution are initially introduced into a heatable 40 liter stirred reactor equipped with a blade stirrer and are heated to 77° C. The following further monomers are then metered in the course of six hours:

5 parts of sodium styrene sulfonate (NaSS) as a 10% solution in water
 5 parts of methyl methacrylate (MMA)
 5 parts of hydroxypropyl acrylate (HPA)

A 2% strength solution of the initiator (ammonium peroxidisulfate, APDS) amounting to 0.31 parts is also metered within 8 hours.

After addition of the total amount of initiator, the reactor is kept at 77° C. for additional 9 hrs.

In the second stage, the reactor temperature is brought down to 53° C., then 154.8 parts of deionized water and 80 parts of vinyl chloride (VC) are added. A total pressure of 6 bar results. The following initiator system is metered within the course of 3.5 hours:

0.17 parts of ammonium peroxidisulfate as a 2% solution in water
 0.026 parts of ascorbic acid (AA) as a 0.3% solution in water.

An additional amount of 0.5 parts MARLON A315 as a 5% solution in water is simultaneously metered within 3 hrs.

After a pressure drop the polymerization is continued for a further 60 min. The resulting dispersion is then cooled down to room temperature, degassed and spray dried to give a white powder.

Example 2 (solution polymerization)

In this experiment, 50 parts of VC are dissolved in 155.3 parts of ethanol-water azeotrope and mixed with 1.6 parts of azobis(isobutyronitrile) (AIBN) as the initiator. After heating up to 50° C. and initiation of the reaction (observation of heat evolution) the following comonomers are metered in the course of 18 hrs:

18.75 parts of hydroxyethyl methacrylate (HEMA)
 18.75 parts of MMBE
 12.5 parts of NaSS.

Simultaneously, 6.2 parts of a 5% solution of AIBN in ethanol are metered in the course of 12 hrs.

24 hours after completion of initiator metering the reactor is cooled down to room temperature. After degassing to remove residual monomer, the fine copolymer suspension is dried in a spray dryer.

Example 3 (emulsion polymerization)

In the first stage 81.4 parts of deionized water, 18.75 parts of maleic acid monobutyl ester (MMBE) and 0.2 parts MARLON A315 (alkyl benzene sulfonate, OXENO Olefinchernie GmbH) as a 15% water solution are initially introduced into a heatable 40 liter stirred reactor equipped with a blade stirrer and are heated to 77° C. The following further monomers are then metered in the course of six hours:

12.5 parts of sodium styrene sulfonate (NaSS) as a 10% solution in water
 18.75 parts of hydroxyethyl methacrylate (HEMA)

A 2% strength solution of the initiator (ammonium peroxidisulfate, APDS) amounting to 0.31 parts is also metered within 6 hours.

After addition of the total amount of initiator, the reactor is kept at 77° C. for additional 11 hrs.

In the second stage, the reactor temperature is brought down to 53° C., then 94.2 parts of deionized water and 50 parts of vinyl chloride (VC) are added. A total pressure of 6 bar results. The following initiator system is metered within the course of 5.5 hours:

0.31 parts of ammonium peroxidisulfate (APDS) as a 2% solution in water
 0.046 parts of ascorbic acid (AA) as a 0.3% solution in water.

An additional amount of 0.5 parts MARLON A315 as a 5% solution in water is simultaneously metered within 3 hrs.

After a pressure drop the polymerization is continued for a further 60 min. The resulting dispersion is then cooled down to room temperature, degassed and spray dried to give a white powder.

Example 4 (emulsion polymerization)

In the first stage 196.6 parts of deionized water, 12. parts of maleic acid monobutyl ester (MMBE) and 0.2 parts MARLON A315 (alkyl benzene sulfonate, OXENO Olefinchernie GmbH) as a 15% water solution are initially introduced into a heatable 250 liter stirred reactor equipped with a blade stirrer and are heated to 77° C. The following further monomers are then metered in the course of six hours:

12.5 parts of sodium styrene sulfonate (NaSS) as a 10% solution in water
 12.5 parts of hydroxypropyl acrylate (HPA)
 12.5 parts of methyl methacrylate (MMA)

A 2% strength solution of the initiator (ammonium peroxidisulfate, APDS) amounting to 0.25 parts is also metered within 8 hours.

After addition of the total amount of initiator, the reactor is kept at 77° C. for additional 11 hrs.

In the second stage, the reactor temperature is brought down to 53° C., then 50 parts of vinyl chloride (VC) are added. A total pressure of 6 bar results. The following initiator system is metered within the course of 8 hours:

0.51 parts of ammonium peroxidisulfate (APDS) as a 2% solution in water
 0.034 parts of ascorbic acid (AA) as a 0.3% solution in water.

An additional amount of 0.5 parts MARLON A315 as a 5% solution in water is simultaneously metered within 8 hrs.

After a pressure drop the polymerization is continued for a further 60 min. The resulting dispersion is then cooled down to room temperature, degassed and spray dried to give a white powder.

The formulations of the aforesaid examples are summarized in Table 1:

TABLE 1

| | | Monomers, Parts | | | | |
|---|---|---|---|---|---|---|
| | | Functional Monomers | | | | |
| | | —COO⁻ | —SO₃⁻ | —OH | | —COOR |
| | | MMBE | NaSS | HPA | HEMA | MMA |
| | | Maleic | Sodium | Hy- | Hy- | Methyl |
| | | acid | styrene | droxy- | droxy | meth- Pro- |
| | | | | propyl | ethyl | cess VC tyl |
| | | | | | | ether fonate |
| | | | | | | late acrylate |
| Run | | monobu- | sul- | acry- | meth- | acrylate |
| 1 | Emul-sion | 80 | 5.0 | 5.0 | 5.0 | 5.0 |
| 2 | Solution | 50 | 18.75 | 12.5 | | 18.75 |
| 3 | Emul-sion | 50 | 18.75 | 12.5 | | 18.75 |
| 4 | Emul-sion | 50 | 12.5 | 12.5 | 12.5 | 12.5 |

Example 5

In a laboratory extruder (GÖTTFERT MEX 30, single screw extruder), dry blends made in a temperature controlled HENSCHEL mixer of the compositions given in Table 2 are processed at a temperature gradient of 160–180° C. along the screw.

TABLE 2

| Components | Tubing 1 | Tubing 2 | Tubing 3 | Tubing 4 | Standard PVC-Tubing |
|---|---|---|---|---|---|
| S-PVC (a) | | 85 | 85 | 85 | 100 |
| Copolymer of Example 1 | 100 | | | | |
| Copolymer of Example 2 (b) | | 15 | | | |
| Copolymer of Example 3 | | | 15 | | |
| Copolymer of Example 4 | | | | 15 | |
| EDENOL B35 (c) | 50 | 18.75 | 15 | 15 | |
| VESTINOL AH (d) | 50 | 41.25 | 45 | 45 | 60 |
| Stabilizer (e) | 1 | 1 | 1 | 1 | 1 |
| Copolymer in compound (%) | 49.8 | 9.3 | 9.3 | 9.3 | 0 |
| Amt. —COOH-Monomer (%) in compound | 2.49 | 1.75 | 1.75 | 1.16 | 0 |
| Amt. —SO₃Na-Monomer (%) in compound | 2.49 | 1.16 | 1.16 | 1.16 | 0 |
| Amt. —OH-Monomer (%) in compound | 2.49 | 1.75 | 1.75 | 1.16 | 0 |
| Biological activity, $k_{app}$ (ml/u · min × 10⁻³) (f) | 4.75 | 4.85 | 5.4 | 4.2 | 1.7 |

(a) Commercial suspension-PVC for medical use (Solvay - SOLVIC 271 GA)
(b) Copolymer synthesized by the solution process
(c) Epoxidized alkyl stearate, epoxy content 4.5–5.5%
(d) Dioctyl phthalate (OXENO Olefinchemie GmbH)
(e) STABIOL CZ 1616/6 (calcium-zinc stearate, HENKEL)
(f) Apparent rate constant of the thrombin-antithrombin reaction (T-AT reaction)

Example 6

In a laboratory extruder (Göttfert MEX 30, single-screw extruder), a mixture of 100 parts of weight of the copolymer obtained from Example 1 is processed with 70 parts by weight of EDENOL B 316 (epoxidized linseed oil, Henkel), 30 parts by weight of dioctyl phthalate and 1 part by weight of calcium/zinc stearate to give tubes having an internal diameter of 3 mm.

The desired bioactive functions are detectable in an even greater amount of the tube surface if the shaping mold is provided with a polar surface rather than only V₂A steel. In this Example, the surface of the shaping mold consisted of: 1.V₂A steel (as comparison), 2. phenol/formaldehyde resin ("polar coating").

Tables 2 and 3 show the different chemical and physical properties of the extrudates. After processing over a phenolic resin-coated extrusion mandrel, substantially more oxygen and sulfur atoms at the surface and a substantially higher polar component of the surface tension are found in comparison with extrusion using uncoated V₂A steel.

TABLE 2

ESCA measurements of VC copolymer tubes from Example 6

| Element | Peak | VC copolymer extruded over metal mandrel (atom %) | VC copolymer extruded over phenolic resin mandrel (atom %) |
|---|---|---|---|
| C | 1 s | 76.5 | 66.6 |
| O | 1 s | 11.5 | 19.9 |
| Cl | 2 p | 11.0 | 6.7 |
| Na | 1 s | 0.4 | 4.9 |
| S | 2 p | 0.3 | 2.8 |

TABLE 3

Measurements of the surface tension of VC copolymer tubes from Example 6

| | Contact angle | | Surface tension | | |
|---|---|---|---|---|---|
| | | | disperse | polar | |
| | H₂O [degrees] | CH₂I₂ [degrees] | component [mN/m] | component [mN/m] | total [mN/m] |
| VC copolymer extruded over metal mandrel | 91 | 35 | 41.5 | 0.6 | 42.1 |
| VC copolymer extruded over phenolic resin mandel | 64 | 60 | 22.4 | 18.0 | 40.4 |

German patent applications 197 08 426.5, filed Mar. 1, 1997, and 197 42 528.3, filed Sep. 26, 1997, are each incorporated herein by reference in their entirety.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for preparing a molding material having anticoagulant properties, comprising:

free radically copolymerizing at least one hydrophobic monomer and at least one hydrophilic monomer having at least one biospecifically active functional group by solution polymerization with subsequent precipitation or by dispersion polymerization to produce the molding material.

2. The process of claim 1, wherein the hydrophobic monomer is a vinyl compound.

3. The process of claim 1, wherein the hydrophobic monomer is styrene, methyl methacrylate, vinyl chloride, or mixtures thereof.

4. The process of claim 1, wherein the hydrophilic monomer has at least at least one biospecifically active functional group selected from the group consisting of hydroxyl, carboxyl, sulfatyl and sulfonyl.

5. The process of claim 1, wherein the hydrophilic monomer is a styrene derivative, a (meth)acryloyl compound, a $^{maleyl}$ compound or a vinyl ether compound.

6. The process of claim 1, wherein the hydrophilic monomer is a styrenesulfonate, hydroxyalkyl (meth)-acrylate, methacrylic acid, maleic monoester or vinyl$(EO)_n$ ether.

7. The process of claim 1, wherein at least a portion of the biospecifically active functions of the hydrophilic monomer are substituted by further biospecifically active functions, said monomer being represented by the formula:

$M—F_1$,
$M—F_2$,
$M—F_3$, or
$M—F_1-F_4$, wherein

M is a radical of the hydrophilic monomer, $F_1$ is an alkyl, aryl or alkyl/arylhydroxyl group, $F_2$ is an alkyl, aryl or alkyl/arylcarboxyl group, $F_3$ is an alkyl, aryl or alkyl/arylsulfonyl group, and $F_4$ is an alkyl, aryl or alkyl/arylphosphatyl group.

8. The process of claim 1, wherein the hydrophilic monomer having at least one biospecifically active functional group is represented by the formula:

$M—F_2—S_1$,
$M—F_3—S_1$,
$M—F_1-F_4—S_1$,
$M—F_1-F_4—S_2$,
$M—F_1-F_4—S_3$, wherein M is a radical of a hydrophilic monomer, $F_1$ is an alkyl, aryl or alkyl/arylhydroxyl group, $F_2$ is an alkyl, aryl or alkyl/arylcarboxyl group, $F_3$ is an alkyl, aryl or alkyl/arylsulfonyl group, $F_4$ is an alkyl, aryl or alkyl/arylphosphatyl group $S_1$ is a radical of an amino acid which is bonded to the carboxyl, sulfonyl or phosphatyl group of the $F_2$, $F_3$ or $F_4$ group via the —$NH_2$ group, $S_2$ is a N-hydroxyethylated purine or pyrimidine base, or sugar radical-purine or sugar radical-pyrimidine base, and $F_4—S_3$ together represent a residue derived from a phospholipid.

9. The process of claim 8, wherein the amino acid is glutamine, threonine, methionine, cysteine, cysteic acid, proline, hydroxylproline, serine, tyrosine, benzoyloxycarbonyl-lysine, tert-butoxycarbonyl-lysine, ε-aminocaproic acid, β-alanine, γ-amino-n-butyric acid, or substituted or unsubstituted δ-amino-n-valeric acid.

10. The process of claim 1, wherein the solvent of the solution polymerization or the dispersing medium of the dispersion polymerization is an alkyl alcohol, water, a ketone, an ether or mixtures thereof.

11. A process for making an article having anticoagulant properties, comprising:

free radically copolymerizing at least one hydrophobic monomer and at least one hydrophilic monomer having at least one biospecifically active functional group by solution polymerization with subsequent precipitation or by dispersion polymerization, thereby producing a molding material; and shaping the molding material having anticoagulant properties obtained into an article.

12. The process of claim 11, wherein the composition further comprises a vinyl chloride homopolymer or copolymer.

13. The process of claim 11, wherein the composition further comprises 5 to 85% by weight of a plasticizer.

14. The process of claim 11, wherein the plasticizer is a mono, di- or tricarboxylic ester of a di- or tricarboxylic or hydroxy-mono-, -di- or -tricarboxylic acid and/or a compound containing epoxy groups wherein the aforesaid component is an epoxidized natural oil, an epoxidized synthetic polymer, an epoxidized fatty acid or esters thereof.

15. The process of claim 11, wherein the shaping step comprises contacting the composition in hot melt from with a shaping mold having a surface tension greater than 50 nM/m at the surface in contact with the composition.

16. The process of claim 14, wherein the shaping mold is coated or lined with metal alloy, a polymer, or a ceramic material.

17. The process of claim 16, wherein said polymer comprises nylon-4, nylon 6, nylon 6,6, or a crosslinked phenol/formaldehyde resin.

18. The process of claim 14, wherein the surface of the shaping mold in contact with the composition is provided with a continuous water/steam gliding film.

19. The process of claim 11, wherein the composition further comprises at least one member selected from the group consisting of stabilizers, lubricants, fillers, dyes and pigments.

* * * * *